Aug. 13, 1957 P. SHAMBURGER Plant Pat. 1,633
ROSE PLANT
Filed July 30, 1956
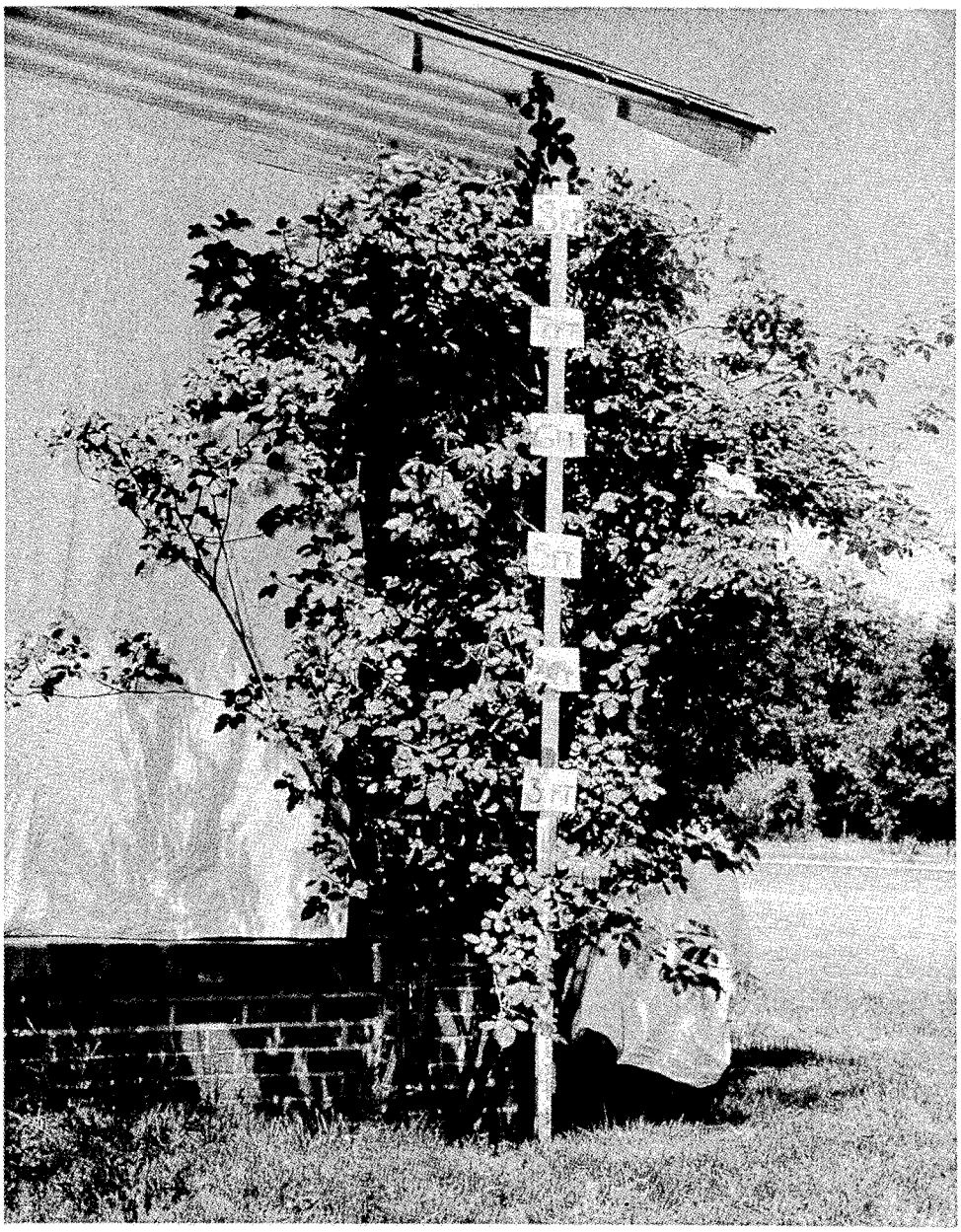
INVENTOR
Paul Shamburger
By: Robb & Robb
ATTORNEYS.

United States Patent Office

Plant Pat. 1,633
Patented Aug. 13, 1957

1,633

ROSE PLANT

Paul Shamburger, Tyler, Tex., assignor to Consolidated Nurseries, Inc., Tyler, Tex., a corporation of Texas Application July 30, 1956, Serial No. 601,099

1 Claim. (Cl. 47—61)

The present invention relates to a new and distinct variety of rose plant of the climbing rose class, which originated as a cultivated sport of the variety "McGredy's Sunset" (Plant Patent No. 317).

This new sport was discovered by me in a cultivated row of budded "McGredy's Sunset" roses which were being grown by me on property under my control at Tyler, Smith County, Texas. During my cultivation of these "McGredy's Sunset" plants, my attention was attracted to one particular plant which exhibited a climbing habit, as distinguished from the normal bush habit of growth of the variety "McGredy's Sunset." Upon closer examination, I found that one of the "McGredy's Sunset" plants had sported, and I thereupon immediately took steps to preserve, asexually reproduce and observe the sport for the purpose of determining whether or not its climbing habit was fixed and was transmissible by asexual reproduction. The climbing habit was fully confirmed by my subsequent observations and by asexual reproduction of the sport by budding, as also performed at Tyler, Texas. Accordingly, I have conclusively established that the climbing habit of growth of the new variety aforementioned comes true to form and is transmissible through succeeding propagations.

Excepting for the climbing habit of my new rose variety, it is otherwise substantially identical in all respects to the parent variety "McGredy's Sunset" and the new sport therefore represents a new and desirable combination of characteristics corresponding to the general characteristics of "McGredy's Sunset," plus its distinctive climbing habit of growth.

The accompanying drawing illustrates in black and white a typical specimen plant of my new variety and depicts in particular its climbing habit of growth.

The following is a brief description of my new variety, with color terminology in accordance with Maerz & Paul Color Dictionary. In those instances where this color dictionary provides a color name, the abbreviation (M. & P.) is employed after such color plate designations. However, in those instances where this color dictionary provides no color name, a color name has been derived from the Flower Color Detector which has been adapted from the Wanscher Flower Chart, published by American Horticultural Council, Inc., of Cornell University at Ithaca, New York, and the notation (detector) is employed after such unnamed Maerz & Paul color plate designations, excepting where general color terms of ordinary dictionary significance are obvious:

Type: Hardy, climber; outdoor; sport; for cut flowers and for garden decoration.
Class: Climbing hybrid tea.
Parentage: Sport of "McGredy's Sunset."
Propagation: Holds its distinguishing characteristics through successive propagations by budding.

*Flower*

Locality where grown and observed: Tyler, Texas.
Flowers borne: Sometimes singly and sometimes several to a stem; in irregular clusters; on stems of normal strength and medium length.
Quantity of bloom: Abundant, outdoors.
Continuity: Continuous.
Fragrance: Strong. Nature—nutty and spicy.
Bud:
*Peduncle.*—Medium length; medium caliper; stiff; almost smooth; with few green hairs. Color—Oasis Green, Plate 20–L–2 (M. & P.).
*Before calyx breaks.*—Size—medium. Form—short, pointed, globular, with foliaceous appendages on the surface of the bud; with slender foliaceous parts extending beyond the tip of the bud equal to ½ of its length. Color—Strong Yellowish Green, Plate 18–L–3 (detector).
*As calyx breaks.*—Color—Light Orange Yellow, Plate 9–L–3 (detector).
*As first petal opens.*—Size—medium. Form—globular. Color: outside—Strong Orange Yellow, Plate 9–L–5 (detector). Inside—Golden Glow Yellow, Plate 9–L–6 (M. & P.). Opening—opens up well.
Bloom:
*Size (when fully open).*—large; from 4½ to 6 inches.
*Petalage.*—Very double; from 85 to 90 petals; arranged regularly.
*Form.*—Full, with high center at first, but becoming open and high-centered, petals being at first loosely rolled outward, but later becoming flat and rolled outward at maturity.
Petals: Thin; soft; with both inside and outside satiny.
*Shape.*—Outside—obovate; scalloped; with apex flat; with one notch. Intermediate—obovate; scalloped; with apex flat, with one notch. Inside—obovate; irregularly scalloped, with one notch.

This description of a newly opened flower was made from a rose grown outdoors in the month of April at Tyler, Texas:

*Color.*—Outer petal: outside surface—Dandelion Yellow, Plate 9–L–4 (M. & P.); inside surface—Golden Glow Yellow, Plate 9–L–6 (M. & P.). Intermediate petal: outside surface—Dandelion Yellow, Plate 9–L–4 (M. & P.); inside surface—Light Reddish Orange, Plate 9–A–9 (detector). Inner petal: outside surface—Strong Orange Yellow, Plate 9–L–5 (detector); inside surface—Light Reddish Orange, Plate 9–A–11 (detector).

This description was made from a rose that was open for three days outdoors in the month of April, at Tyler, Texas.

*Color.*—Outer petal: outside surface—Light Orange Yellow, Plate 9–I–4 (detector); inside surface—Golden Corn Yellow, Plate 9–I–6 (M. & P.). Inner petal: outside surface—Light Orange Yellow, Plate 9–I–4 (detector); inside surface—Golden Corn Yellow, Plate 9–I–6 (M. & P.).
*General color effect.*—Newly opened flower—Princeton Orange, Plate 9–K–11 (M. & P.). 3-days open—Light Yellowish Orange, Plate 9–H–7 (detector).
*Behavior.*—Drop off cleanly; fading yellow; normal.
*Flower longevity.*—On bush in garden—5 days in April. Cut roses griwn outdoors and kept at living-room temperatures—4 days in April.

*Reproductive organs*

Stamens: Medium number; arranged regularly; mixed with petaloids. Color—Yellow, Plate 9–L–4 (M. & P.).

Filaments: Long; many with anthers. Color—Golden Glow Yellow, Plate 9–L–6 (M. & P.).

Anthers: Medium size; open at various times. Color—Deep Chrome Yellow, Plate 9–L–7 (M. & P.).

Pollen: Moderate. Color—Golden Glow Yellow, Plate 9–L–6 (M. & P.).

Pistils: Medium number.

Styles: Uneven; short; medium caliper; bunched.

Stigma: Color—Sunflower Yellow, Plate 9–L–4 (M. & P.).

Ovaries: Enclosed in calyx.

Hips: Globular; very smooth; walls thick and fleshy. Color—Lettuce Green, Plate 20–L–5 (M. & P.).

Sepals: Permanent; moderately long; spear-shaped; curled.

Seeds: Few; medium size.

*Plant*

Foliage:

*Leaves.*—Compound of 5 leaflets; normal abundance; medium size; moderately heavy; glossy.

*Leaflets.*—Shape — oval. Apex — acute. Base—round. Margin—serrate.

*Color.*—Mature: upper surface—Moderately Dark Green, Plate 24–L–6 (M. & P.); under surface—Light Green, Plate 23–E–5 (M. & P.). Young: upper surface—Green-Bronze, Plate 16–H–6 (M. & P.); under surface—Light Bronze, Plate 16–E–8 (M. & P.).

*Rachis (the supporting stem of the compound leaf).*—Medium size. Upper side—smooth. Under side—smooth.

*Stipules.*—Medium length; moderate width; with very short points turning out at an angle of less than 90°.

*Disease resistance.*—Somewhat subject to blackspot, but more resistant thereto than its parent variety, and readily controlled by use of good fungicide; no mildew, however, observed; these characteristics determined by comparison with other varieties grown under comparable cultural conditions at Tyler, Texas.

Growth:

*Habit.*—Trailing and climbing; much-branched.

*Growth.*—Vigorous; attains height of from 10 to 12 feet in approximately 2 years.

*Canes.*—Medium caliper.

*Main stems.*—Color—Beetle Green, Plate 16–J–6 (M. & P.). Thorns—several; medium length; hooked downward; with long, narrow base. Prickles—few; color—Beetle-Green, Plate 16–J–6 (M. & P.). Hairs—none.

*Branches.*—Color—Shadow Green, Plate 20–J–3 (M. & P.). Thorns—few; medium length; hooked downward; with long, narrow base. Prickles—none. Hairs—none.

*New shoots.*—Color—Silver Fern Green, Plate 14–J–2 (M. & P.). Thorns—very few; moderate length; hooked downward; with long, narrow base. Prickles—few; color—reddish. Hairs—none.

I claim:

A new and distinct variety of rose plant of the climber class, substantially as herein shown and described, characterized particularly as to novelty by its general similarity to the variety "McGredy's Sunset" (Plant Patent No. 317), while differing from the latter by its climbing habit and rapid growth.

No references cited.